United States Patent [19]

Roscher et al.

[11] Patent Number: 5,066,365
[45] Date of Patent: Nov. 19, 1991

[54] PROCESS FOR THE ISOLATION OF VINYL ACETATE BY DISTILLATION

[75] Inventors: Günter Roscher, Kelkheim; Karl-Heinz Schmidt, Idstein/Taunus; Klaus Eichler, Eschborn; Peter Hörstermann, Königstein/Taunus; Reinhard Gradl, Erftstadt; Horst Langner, Hattersheim, all of Fed. Rep. of Germany

[73] Assignee: Hoechst Aktiengesellschaft, Frankfurt am Main, Fed. Rep. of Germany

[21] Appl. No.: 597,572

[22] Filed: Oct. 15, 1990

[30] Foreign Application Priority Data

Oct. 17, 1989 [DE] Fed. Rep. of Germany ....... 3934614

[51] Int. Cl.$^5$ .................. B01D 3/00; C07C 67/54
[52] U.S. Cl. .................. 203/042; 203/71; 203/81; 203/82; 203/87; 203/Dig. 10; 203/Dig. 19; 560/248
[58] Field of Search ............ 203/14, Dig. 10, Dig. 19, 203/42, 71, 73, 74, 78, 80, 81, 84, 87, 99, 39, Dig. 9, 98; 560/248

[56] References Cited

U.S. PATENT DOCUMENTS

| 3,404,177 | 10/1968 | Baba et al. ............... 560/248 |
| 3,438,870 | 4/1969 | Roscher et al. ............ 203/14 |
| 3,692,636 | 9/1972 | Huguet .................... 203/71 |
| 3,905,875 | 9/1975 | Kronig et al. ............. 203/14 |
| 4,156,632 | 5/1979 | Roscher et al. ............ 203/14 |
| 4,818,347 | 4/1989 | Roscher et al. ............ 203/DIG. 9 |

FOREIGN PATENT DOCUMENTS

| 28362 | 5/1981 | European Pat. Off. ....... 560/248 |
| 2945913 | 6/1981 | Fed. Rep. of Germany ..... 560/248 |

Primary Examiner—Wilbur Bascomb, Jr.

[57] ABSTRACT

The invention relates to a process for the isolation of vinyl acetate which involves not combining the bottom product of the recylced gas washings with the water-saturated vinyl acetate but rather introducing it to further multiple distillation columns from the gas mixture formed in the reaction of ethylene with acetic acid and oxygen over catalysts containing palladium or palladium compounds in the gas phase.

6 Claims, 1 Drawing Sheet

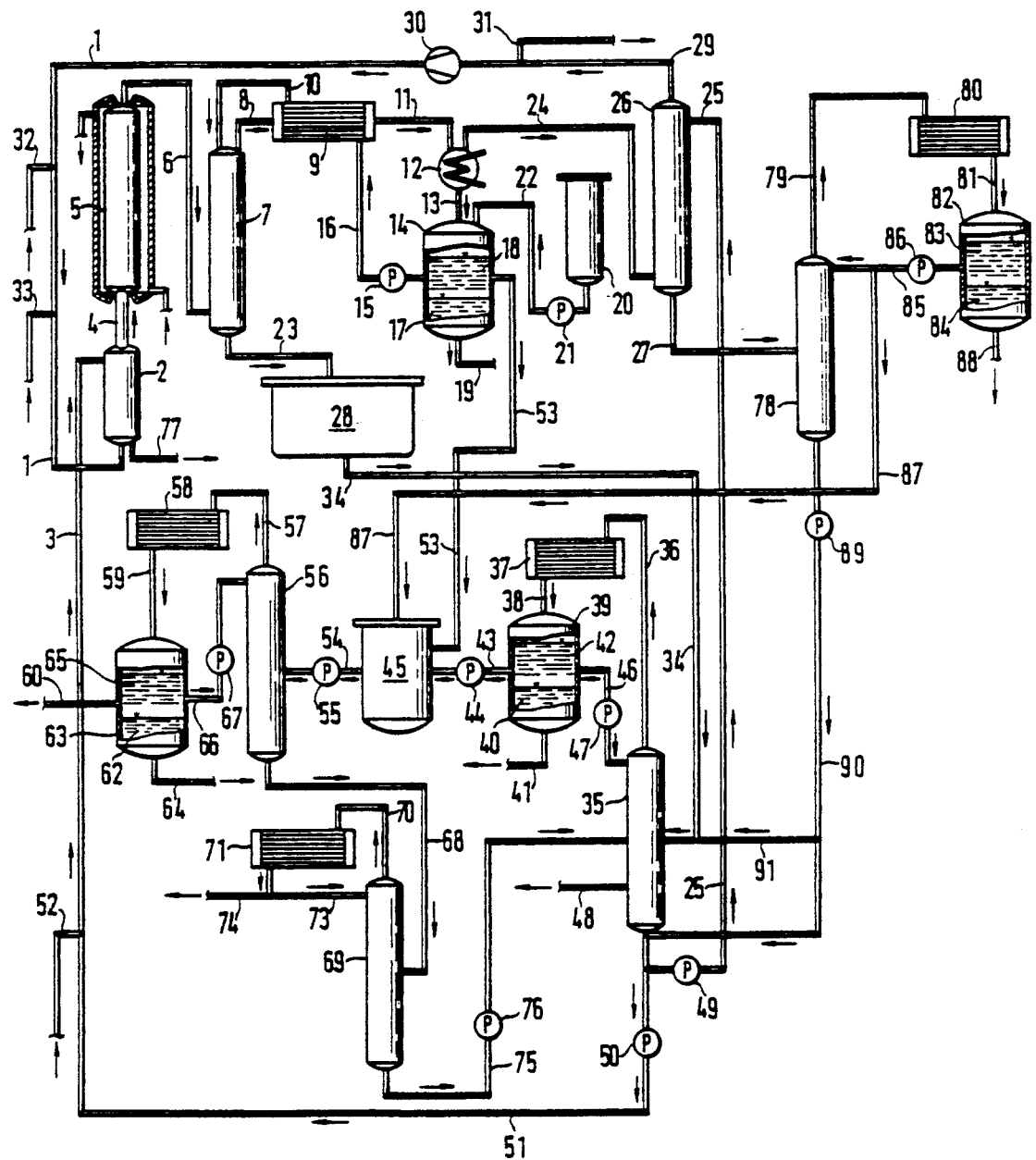

PROCESS FOR THE ISOLATION OF VINYL ACETATE BY DISTILLATION

DESCRIPTION PROCESS FOR THE ISOLATION OF VINYL ACETATE

The preparation of vinyl acetate by reacting ethylene with acetic acid and oxygen or oxygen-containing gases over fixed bed catalysts in the gas phase is already known. The reaction is in general carried out at pressures of 1 to 25 bar at temperatures of 100° to 250° C. Suitable catalysts contain a noble metal portion and an activator portion. The noble metal portion comprises palladium and/or compounds thereof; in addition, gold or compounds thereof can be present. The activator portion comprises compounds of elements of main group 1 and/or main group 2 and/or cadmium. These active components are applied to supports in finely divided form, silica or alumina being in general used as the support material.

In general, the palladium content in the catalyst is between 0.5 and 5 % by weight.

If gold or one of its compounds is used, it is added in an amount of 0.01 to 4 % by weight.

Each individual activator is in general also added in an amount of 0.01 to 4 % by weight. In all three percentages given, the metal content of the component is in each case based on the overall weight of the supported catalyst. The following catalysts are preferred:

Palladium/alkali metal/cadmium and palladium/gold/alkali metal, it being possible for palladium and gold to be present in the ready-to-use catalyst as metals or compounds and potassium being preferred as the alkali metal (in the form of a carboxylate). The catalysts palladium acetate/potassium acetate/cadmium acetate and palladium acetate/barium acetoaurate/ potassium acetate are particularly preferred. In the multi-step catalytic process, vinyl acetate and water are formed in equimolar amounts, as shown in the following net equation:

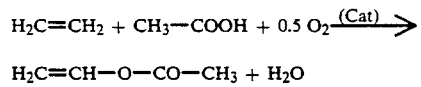

$$H_2C{=}CH{-}O{-}CO{-}CH_3 + H_2O$$

The complete oxidation of ethylene, which cannot be avoided altogether, gives $CO_2$ and water:

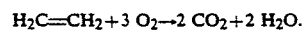

Therefore more than 1 mole of water is formed per mole of vinyl acetate; in general, the weight of the water makes about one fourth of the weight of the vinyl acetate formed.

Apart from $CO_2$, other by-products are also formed in small amounts, which also include ethyl acetate in an amount of about 1,000–2,000 ppm by weight, relative to the vinyl acetate formed. Ethyl acetate may be present in pure vinyl acetate only in an amount of at most 150 ppm by weight. Previously, a large amount of energy had been necessary to separate off the ethyl acetate. Therefore, a process had to be found which produces vinyl acetate in pure form and free of ethyl acetate and other by-products with less expenditure of energy than before.

The invention now relates to a process by means of which vinyl acetate can be isolated with less consumption of energy and can in particular be freed from ethyl acetate.

The mixture used for the reaction contains many times the amount of ethylene required by stoichiometry. Accordingly, the ethylene conversion of about 10 % is relatively low and the unconverted ethylene has to be recycled into the reaction zone. The vinyl acetate is usually separated off from the mixture of the reaction product formed as a gas in a multi-step process. In the process according to German Offenlegungsschrift 3,422,575 (=U.S. Pat. No. 4,818,347), the hot gas mixture leaving the vinyl acetate reactor and substantially comprising unconverted ethylene, unconverted acetic acid, unconverted oxygen, nitrogen, argon, vinyl acetate, water of the reaction, $CO_2$ and ethyl acetate is passed into a distillation column operating without any additional heating, the so-called pre-dehydrating columns. The gas mixture leaving at the head of this column is cooled to $-20°$ to $+50°$ C., leading to partial condensation. The condensate separates into two phases, an organic and an aqueous one. The aqueous phase is removed, and the organic phase is reintroduced completely or in part as reflux at the head of the pre-dehydration column. The uncondensed portion of the head vapor of this column still contains gaseous vinyl acetate, which is washed out of the gas mixture in a washing column operated with acetic acid as the washing liquid. The remaining gas is recycled into the reactor. At the bottom of the predehydration column, a mixture is formed comprising vinyl acetate, acetic acid and about half of the water of the reaction and by-products. The other half of the water of the reaction has already been separated off without adding any energy and forms the aqueous phase of the condensate formed in the abovementioned cooling of the head vapor of the pre-dehydration column.

The bottom product of the pre-dehydration column is separated in a second column in A) water-saturated vinyl acetate as the head product, B) a side stream containing ethyl acetate which is removed and C) a bottom product which is recycled into the system in the form of recycled acetic acid. The water-saturated vinyl acetate A) is then combined with the bottom product of the washing column, and the mixture is worked up in two further columns.

Surprisingly, it has now been found that it is more advantageous to combine the bottom product of the recycled gas washings not directly with the water-saturated vinyl acetate A), but first introduce it into a further column which gives a vinyl acetate/water azeotrope as the head product and aqueous acetic acid (which is recycled into the abovementioned second column or into the cycle gas washings or directly into the reaction zone) as the bottom product. After the aqueous phase formed by cooling has been separated off, the head product is dried together with the water-saturated vinyl acetate A) (head product of the second column) in a further column, and pure vinyl acetate is distilled in a last column at the column head. This method of workup has a similarly low expenditure of distillation energy as the one described in German Offenlegungsschrift 3,422,575 (=U.S. Pat. No. 4,818,347) but has the advantage that the overall number of column plates necessary for workup is smaller, which means significantly reduced investment costs.

The invention accordingly relates to a process for the isolation of vinyl acetate from a gas mixture containing vinyl acetate, ethyl acetate, acetic acid, water and carbon dioxide which is formed in the reaction of ethylene with acetic acid and oxygen in a reaction zone in the gas phase over catalysts containing palladium or palladium compounds, in which process a) the gas mixture leaving the reaction zone is passed into a first distillation column, b) the gas mixture leaving at the head of the first distillation column is cooled to −20° to +50° C., as a result of which the condensate formed separates into an aqueous and an organic phase, c) the aqueous phase formed in step b) is removed, d) the organic phase formed in step b) is reintroduced completely or in part as reflux at the head of the first distillation column used in step a) and any portion of the organic phase not used as reflux is removed, e) the gas not condensed in step b) and containing vinyl acetate is washed in a washing column with at least 90% aqueous acetic acid to give an acetic acid solution containing vinyl acetate at the bottom, f) the bottom product of step a) containing vinyl acetate, ethyl acetate, acetic acid and water is passed to a second distillation column and a sidestream containing ethyl acetate is removed from a concentration zone above the bottom thereof, g) the bottom product of step f) containing acetic acid and water is used completely or in part for the gas washing in step e), h) the head vapor of step f) is cooled, as a result of which the condensate formed separates into an aqueous and an organic phase, i) the aqueous phase formed in step h) is removed, k) a portion of the organic phase formed in step h) is reintroduced as reflux at the head of the second distillation column used in step f), l) the remaining portion of the organic phase formed in step h) is removed, which comprises m) introducing the bottom product of the washing column used in step e) into a third distillation column, n) recycling the bottom product of the third distillation column used in step m) into the second distillation column used in step f) or into the washing column used in step e) or into the reaction zone, o) cooling the head vapor of step m), as a result of which the condensate formed separates into an aqueous and an organic phase, p) removing the aqueous phase formed in step o), q) re-introducing a portion of the organic phase formed in step o) as reflux at the head of the third distillation column used in step m), r) passing the remaining portion of the organic phase formed in step o) together with the remaining organic phase removed in step l) and together with any remaining organic phase removed in step d) into a fourth distillation column, s) cooling the head vapor of step r), as a result of which the condensate formed separates into an aqueous and an organic phase, t) removing the aqueous phase formed in step s), u) re-introducing the organic phase formed in step s) completely or in part as reflux at the head of the fourth distillation column used in step r) and removing any portion of the organic phase not used as reflux for separating off the low-boiling components, v) passing the bottom product from step r) into a fifth distillation column, w) removing pure vinyl acetate at the head of the fifth distillation column used in step v).

BRIEF DESCRIPTION OF THE DRAWING

The sole Figure of the Drawing is a schematic representation illustrating an apparatus which can be used to carry out the process of this invention.

DETAILED DESCRIPTION

In step a), the gas mixture leaving the reaction zone is preferably first cooled to about 115°–130° C. (which does not yet lead to condensation of the liquefiable portions) by counter-current heat exchange with the colder recycle gas (which is thereby heated and then recycled into the reaction) and only then introduced into the first distillation column.

The amount of the organic phase formed in step b) depends on up to which temperature the gas mixture is cooled in this step. The portion of the organic phase from step b) which is not used as reflux in step d) is passed in step r) (together with the organic phase from step h) and o) not used as reflux for the second and third distillation column) into the fourth distillation column. The cooling temperature in step b) and the portion of the organic phase formed in b) which is used as reflux in step d) are preferably selected such that a minimum amount of vinyl acetate but, if possible, the entire ethyl acetate are present in the bottom product from step a). This means that about 20 to 50 % by weight of the vinyl acetate are present in this bottom product. The remaining 50–80% by weight of the vinyl acetate are then present in part in the acetic acid solution formed in step e) and in part in the portion of the organic phase formed in step b) which is not used as reflux in step d).

For the gas washing of step e), at least part of the bottom product of the second distillation column (step f)) is used, and additionally the bottom product of the third distillation column formed in step m) can be used; both bottom products are mainly composed of acetic acid and contain at most 10% by weight of water. A portion of the bottom products mentioned which is not required in step e) is preferably recycled into the reactor, after a small portion has been discharged for removing high-boiling components and polymers.

In step k), preferably only such an amount of the organic phase formed in step h) is reintroduced as reflux that the head vapor of the second distillation column contains a minimum amount of acetic acid and ethyl acetate. The portion of the organic phase which is not required for this purpose is introduced into the fourth distillation column according to step r).

In step q), preferably such an amount of the organic phase formed in step o) is reintroduced as reflux at the head of the third distillation column that a minimum amount of vinyl acetate is obtained in the bottom thereof.

In step u), the organic phase formed in step s) is preferably not used in its entirety as reflux for the fourth distillation column but a portion sufficient for separating off the low-boiling components is removed.

The surprising advantage of the process according to the invention consists in the energy-saving separation of the ethyl acetate formed in the vinyl acetate reaction as a by-product with less complicated apparatus than before (German Offenlegungsschrift 3,422,575 and U.S. Pat. No. 4,818,347): in the pre-dehydration column used in step a) (the first distillation column), a portion of the vinyl acetate is already separated off in a form free of ethyl acetate. The reason is that virtually all the ethyl acetate remains in the bottom of the pre-dehydration column, while the portion of the vinyl acetate not condensed in step b) (which is obtained in step e) in the form of an acetic acid solution) and also any remaining organic phase removed in step d) contain virtually no ethyl acetate, thus making an energy-consuming removal of ethyl acetate from the vinyl acetate partial streams unnecessary. This workup is achieved in the process according to the invention by means of a smaller number of column plates than according to German Offenlegungsschrift 3,422,575.

The process according to the invention is illustrated by means of the Figure.

The gas mixture comprising ethylene, oxygen and $CO_2$ (=recycled gas) is passed via line (1) into an acetic acid evaporator (2) designed as a bubble column, in which the gas stream is charged with acetic acid fed in via line (3). The gas mixture leaving the acetic acid evaporator (2) is fed into the reactor (5) via a steam-heated line (4). This reactor comprises a reaction tube of 5.60 m in length and 32 mm in internal diameter surrounded by a jacket. The removal of the heat of the reaction is effected by means of boiling water under pressure in this jacket. The reaction tube is filled with the catalyst. The gas mixture leaving the reactor (5) mainly comprising ethylene, acetic acid, vinyl acetate, water, carbon dioxide, oxygen and inert gases, such as, for example, nitrogen and argon, is passed via line (6) into the first distillation column, the pre-dehydration column (7). Column (7) has a length of 2.5 m and a diameter of 50 mm. It is filled with packings made of rolled-up stainless steel wire mesh (so-called Goodloe packings). The gas mixture leaving column (7) at the head enters a heat exchanger (9) via line (8), where it is brought into counter-current heat exchange with the reflux which enters via line (16) and is recycled into column (7) via line (10). From the heat exchanger (9), the gas mixture enters a water-cooled condenser (12) via line (11), where it is cooled to about 35° C. The liquefied portions enter tank (14) via line (13), where they are collected. A portion of liquid exceeding a certain level in the collecting tank (14) is pumped back into the predehydration column (7) by means of pump (15) via line (16), heat exchanger (9) and line (10). After a certain period of time, the condensate formed in the collecting tank (14) separates into two phases (17) and (18); from now on, the aqueous phase (17) is discharged via line (19) and only the organic phase (18) is pumped back as reflux into the head of the pre-dehydration column (7) completely or in part via line (16), heat exchanger (9) and line (10). Stabilizer solution is pumped from storage tank (20) via pump (21) and line (22) into the collecting tank (14). The liquid formed at the bottom of the predehydration column (7) which mainly comprises vinyl acetate, acetic acid and water and almost the entire ethyl acetate is discharged into tank (28) via line (23). The gas mixture leaving condenser (12) via line (24) is freed of uncondensed vinyl acetate portions in the washing column (26) charged with acetic acid via line (25); the bottom product of column (26) enters column (78) via line (27). The residual gas leaving the washing column (26) via line (29)(ethylene, unconverted oxygen and $CO_2$ formed as by-product) is recycled via line (1) and the acetic acid evaporator (2) into the reactor (5) by means of a recycled gas compressor (30). A portion of the recycled gas is removed as waste gas via line (31) in order to discharge inert components. Fresh ethylene is fed in via line (32) and fresh oxygen via line (33). The mixture from tank (28) is passed into the second distillation column (35) via line (34). The head vapor of column (35) is passed into condenser (37) via line (36) and condensed there. The condensate entering tank (39) via line (38) separates into an aqueous phase (40), which is discharged via line (41), and an organic phase (42), one portion of which is fed into tank (45) via line (43) and pump (44), while the other portion is recycled into column (35) via line (46) and pump (47) and serves there as reflux to prevent acetic acid and ethyl acetate from being carried over to the head product. The ethyl acetate present in the mixture in tank (28) and entering column (35) via line (34) is removed via line (48) from a concentration zone above the bottom of column (35). The bottom product of column (35) contains acetic acid, at most 10 % by weight of water and small amounts of high-boiling components and polymers and only traces of vinyl acetate and ethyl acetate.

The aqueous acetic acid from the bottom of column (35) is divided. The portion required for the acetic acid washing in step e) is fed into the washing column (26) via pump (49) and line (25). The remainder is again fed into the acetic acid evaporator (2) via pump (50), line (51) and line (3). Depending on the design of the washing column (26) and the temperature of the gas to be washed, varying amounts of acetic acid are required as washing liquid. The aqueous acetic acid drained from the bottom of column (35) is therefore divided accordingly. Fresh acetic acid corresponding to the amount of acetic acid consumed in the reaction is fed into the acetic acid evaporator (2) via lines (52) and (3). The bottom product of column (26) is fed into the third distillation column (78) via line (27). A portion of the organic phase (42) from tank (39) is fed into tank (45) via line (43) and pump (44). In addition, the remainder of the organic phase (18) is passed from collecting tank (14) via line (53) to tank (45), in case not the entire organic phase (18) is used as reflux in the pre-dehydration column (7). The liquid in tank (45) is passed to the fourth distillation column (56) via line (54) and pump (55). The head vapor of column (56) is passed to condenser (58) via line (57); the condensate formed is passed to tank (63) via line (59). In tank (63), it separates into two phases, an aqueous phase (62) and an organic phase (65). The aqueous phase (62) is discharged via line 64. The organic phase (65) is reintroduced as reflux at the head of column (56) via line (66) and pump (67). A small partial stream of the organic phase (65) is discharged via line (60) for separating of the lower-boiling components. The virtually water-free bottom product of column (56) is passed on via line (68) (see below). The head vapor of column (78) is fed into condenser (80) via line (79). The condensate formed runs into tank (82) via line (81). The condensate forms an organic phase (83) and an aqueous phase (84). The aqueous phase (84) is discharged via line (86). The organic phase (83) is in part reintroduced as reflux at the head of column (78) via line (85) and pump (86). A portion is discharged into tank (45) via line (87). The bottom product of column (78) is in general combined with the bottom product of column (35) via pump (89) and line (90), and then pumped to the acetic acid washing solution (26) or into the acetic acid evaporator (2). However, it can also be passed into column (35) via line (91). The virtually water-free vinyl acetate formed at the bottom of column (56) is passed to the fifth distillation column (69) via line (68). The head vapor of this column enters condenser (71) via line (70). The condensate formed is pure vinyl acetate which is virtually free of ethyl acetate. A very small portion of this vinyl acetate is recycled as reflux into column (69) via line (73). Pure vinyl acetate is discharged via line (74). The bottom product of column (69) containing polymers, high-boiling components and vinyl acetate/ethyl acetate/acetic acid is recycled into column (35) via line (75) and pump (76). A partial stream is removed from the acetic acid evaporator (2), into which finally all high-boiling components and polymers are recycled, via line (77) to discharge the polymers.

EXAMPLE

The experiment which follows was carried out in the apparatus described above and shown in FIG. 1. The reactor (5) was filled with 4.4 l of a known vinyl acetate catalyst containing 2.3% by weight of palladium, 2% by weight of potassium and 1.9% by weight of cadmium, each in the form of their acetates on a silica support (beads of 4-6 mm in diameter). 12 Nm$^3$ per hour of a mixture containing about 69% by volume of ethylene, 24% by volume of carbon dioxide and 7% by volume of oxygen were introduced into the acetic acid evaporator (2). The amount of acetic acid fed to the acetic acid evaporator (2) via line (3) was such that 4.83 kg of acetic acid evaporated in it. To discharge the high-boiling components and the polymers, 0.5 kg of material per hour was discharged from the acetic acid evaporator (2) via line (77). The gas streaming into the reactor was preheated to 155° C. in line (4). A superatmospheric pressure of 8 bar (9 bar absolute) was established at the reactor inlet (5), and the temperature at the reactor outlet was adjusted to 160° C. via the pressure on the boiling water cooling system in the outer jacket of the reactor. The temperature of the reaction gases at the pre-dehydration column (7) inlet was no more than 130° C., due to heat radiation of line (6). The gas mixture leaving the pre-dehydration column (7) at the head was cooled to 35° C. in condenser (12). In tank (14), 9 kg per hour of organic phase (18) were formed, which were recycled into the pre-dehydration column (7) via pump (15) and heat exchanger (9) 350 g per hour of an aqueous phase (17) containing 3% by weight of vinyl acetate, 0.1% by weight of acetic acid and 0.05% by weight of acetaldehyde were removed from tank (14). At the bottom of pre-dehydration column (7), in which a head temperature of 80° C. and a bottom temperature of 90° C. were reached, 4 kg of a mixture comprising 74% by weight of acetic acid, 7.5% by weight of water, 17.5% by weight of vinyl acetate, 0.05% by weight of ethylidene diacetate, 0.06% by weight of ethyl acetate, 0.1% by weight of acetaldehyde and 0.05% by weight of high-boiling components and polymers were formed per hour. For stabilization, 15 ml of a solution of 2.5% by weight of p-benzoquinone in vinyl acetate were pumped per hour from storage tank (20) to tank (14).

The remaining gas from the condenser (12) was passed into the washing column (26) via line (24). 3.1 kg per hour of water-containing acetic acid were pumped from the bottom of column (35) via line (25) into the head of the washing column (26). At the bottom of the washing column (26), 5 kg of a mixture comprising 57.6% by weight of acetic acid, 5.1% by weight of water, 37% by weight of vinyl acetate, 0.02% by weight of acetaldehyde and 30 ppm by weight of ethyl acetate were formed per hour.

The gas leaving the washing column (26) was recycled into the acetic acid evaporator (2) via line (29) and the

We claim:

1. A process for the isolation of vinyl acetate from a gas mixture containing vinyl acetate, ethyl acetate, acetic acid, water and carbon dioxide and being formed in the reaction of ethylene with acetic acid and oxygen in a reaction zone in the gas phase over catalysts containing palladium or palladium compounds, in which process a) the gas mixture leaving the reaction zone is passed into a first distillation column yielding a gas mixture as a head product, and a product containing vinyl acetate, ethyl acetate, acetic acid, and water as a bottom product, b) the gas mixture leaving at the head of the first distillation column is cooled to −20° C. to + 50° C., as a result of which a condensate is formed from some portion of said gas mixture and then separates into an aqueous and an organic phase, while some portion of said gas mixture is not condensed, c) the aqueous phase formed in step b) is removed, d) the organic phase formed in step b) is reintroduced completely or in part as reflux at the head of the first distillation column used in step a) and any portion of the organic phase not used as reflux is removed, e) said portion of the gas mixture not condensed in step b) and containing vinyl acetate is washed in a washing column with at least 90% aqueous acetic acid to give an acetic acid solution containing vinyl acetate at the bottom, f) the bottom product of step a) containing vinyl acetate, ethyl acetate, acetic acid and water is passed to a second distillation column yielding a head vapor product and a bottom product and a side-stream containing ethyl acetate is removed from a concentration zone above the bottom thereof, g) the bottom product of step f) containing acetic acid and water is used completely or in part for the gas washing in step e), h) the head vapor of the step f) is cooled, as a result of which a condensate is formed and then separates into an aqueous and an organic phase, i) the aqueous phase formed in step h) is removed, k) a portion of the organic phase formed in step h) is reintroduced as reflux at the head of the second distillation column used in step f), l) the remaining portion of the organic phase formed in step h) is removed, which comprises m) introducing the bottom product of the washing column used in step e) into a third distillation column yielding a bottom product and a head vapor product, n) recycling the bottom product of the third distillation column used in step m) into the second distillation column used in step f) or into the washing column used in step e) or into the reaction zone, o) cooling the head vapor product of stem m), as a result of which a condensate is formed and then separates into an aqueous and an organic phase, p) removing the aqueous phase formed in step o), q) re-introducing a portion of the organic phase formed in step o) as reflux at the head of the third distillation column used in step m), r) passing the remaining portion of the organic phase formed in step o) together with the remaining organic phase removed in step l) and together with any remaining organic phase removed in step d) into a fourth distillation column yielding a head vapor product and a bottom product, s) cooling the head vapor of step r), as a result of which a condensate is formed and then separates into an aqueous and an organic phase containing low-boiling components, t) removing the aqueous phase formed in step s), u) re-introducing the organic phase formed in step s) completely or in part as reflux at the head of the fourth distillation column used in step r) and removing any portion of the organic phase not used as reflux for separating off the low-boiling components, v) passing the bottom product from step r) into a fifth distillation column, w) removing pure vinyl acetate at the head of the fifth distillation column used in step v).

2. The process as claimed in claim 1, wherein in step a) the gas mixture leaving the reaction zone is first cooled to about 115°–130° C. by counter-current heat exchange with a colder recycled gas and only then passed into the first distillation column.

3. The process as claimed in claim 1, wherein the cooling temperature in step b) and the portion of the organic phase formed in b) which is used as reflux in step d) are selected such that an amount ranging from 20% to 50% by weight of vinyl acetate but a maximum of the entire ethyl acetate are present in the bottom product of step a).

4. The process as claimed in claim 1, wherein in step k) an amount of the organic phase formed in step h) is reintroduced as reflux, said amount being limited such that the amount of acetic acid and ethyl acetate in the head vapor product of the second distillation column is minimized and the portion of the organic phase which is not required for this purpose is introduced into the fourth distillation column according to step r).

5. The process as claimed in claim 1, wherein in step q) the organic phase formed in step o) which is reintroduced as reflux at the head of the third distillation column is reintroduced in an amount such that the amount of vinyl acetate obtained in the bottom of said column is minimized.

6. The process as claimed in claim 1, wherein step u) the organic phase formed in step s) is not used in its entirety as reflux for the fourth distillation column but a portion sufficient for separating off the low-boiling components is removed.

* * * * *